United States Patent [19]
Wilson et al.

[11] Patent Number: 6,165,177
[45] Date of Patent: Dec. 26, 2000

[54] ALIGNMENT GUIDE FOR INSERTION OF STEM PROSTHESIS

[75] Inventors: Stephen Wilson, Raynham, Mass.; Anthony P. Sanders, Salt Lake City, Utah; Michael S. Varieur, Attleboro; Mark Allan Manasas, South Easton, both of Mass.; Andrew Ira Spitzer, Los Angeles, Calif.

[73] Assignee: Depuy Orthopaedics, Inc., Warsaw, Ind.

[21] Appl. No.: 09/220,717

[22] Filed: Dec. 24, 1998

[51] Int. Cl.$^7$ ................ A61B 17/58; A61F 2/32
[52] U.S. Cl. ............ 606/100; 606/99; 623/22.12
[58] Field of Search ................ 606/99, 100, 86; 623/22, 22.12

[56] References Cited

U.S. PATENT DOCUMENTS

| | | | |
|---|---|---|---|
| 4,993,410 | 2/1991 | Kimsey | 606/100 |
| 5,064,427 | 11/1991 | Burkinshaw | 606/99 |
| 5,169,401 | 12/1992 | Lester et al. | 606/99 X |
| 5,171,324 | 12/1992 | Campana et al. | 623/23 |
| 5,190,550 | 3/1993 | Miller et al. | 606/99 X |
| 5,476,466 | 12/1995 | Barrette et al. | 606/99 X |
| 5,514,136 | 5/1996 | Richelsoph | 606/99 |
| 5,601,567 | 2/1997 | Swajger et al. | 606/102 |
| 5,888,208 | 3/1999 | Ro | 623/23 |
| 5,888,245 | 3/1999 | Meulink et al. | 623/23 |
| 5,989,259 | 11/1999 | Penenberg et al. | 606/99 |

FOREIGN PATENT DOCUMENTS

| | | | |
|---|---|---|---|
| 0 850 610 A2 | 7/1998 | European Pat. Off. | A61F 2/46 |
| 2615097 | 11/1988 | France | 606/99 |
| WO 97 27828 | 8/1997 | WIPO | A61F 2/32 |

*Primary Examiner*—Jeffrey A. Smith
*Attorney, Agent, or Firm*—Nutter, McClennen & Fish, LLP

[57] ABSTRACT

A method and tool for inserting a prosthetic stem component in an aligned position into a prepared bone cavity. The bone is prepared by removing bone material from the bone canal and preferably also machining an entry opening of a predetermined shape and desired orientation in the bone, or marking the plane of the joint on the bone end. The tool includes an upper component that engages the top of the prosthesis stem to fix its rotational alignment, and an arm that extends to the opening in the bone and is aligned at its distal end. The upper component rides along the arm, and orients the stem with respect to the bone as the stem is inserted. The tool may include a lower element that engages the machined or marked bone and holds the arm to orient the head of the prosthesis. Optionally, the lower element may guide the distal stem. Alternatively, the guide may include an arm that simply points to, contacts or fastens at the bone end, orienting the prosthesis insertion without sighting errors. In a pointer or pin assembly which extends to an alignment point on the proximal femur, the upper portion may clamp to the femoral component head or neck, and may include a sliding bushing, that allows the guide to remain rigidly coupled as the stem is progressively advanced in the femoral canal. Articulation may be provided by a pivot mounting of the arms and bushing, and the bushing may swivel as it rides along a post, rail or pin, the lower end of which remains pointed to, or driven into, an alignment mark scribed at the medial periphery of the cut surface of the proximal femur. Alternatively, a lower alignment body may fit against a machined bone surface to fix the orientation of a linking arm in one plane, with a sliding coupling to the upper part of the prosthesis to maintain that orientation as the stem is driven down into contact with the prepared bone surface.

19 Claims, 4 Drawing Sheets

ALIGNMENT GUIDE FOR INSERTION OF STEM PROSTHESIS

REFERENCE TO RELATED APPLICATION

This patent application is related to co-pending U.S. patent application Ser. No. 09/130,396 (pending) of inventors Michael S. Varieur et al entitled Alignment Guide for Slotted Prosthetic Stem, bearing attorney docket number 22675-146 and filed in the Patent and Trademark Office on Aug. 6, 1998. That application is hereby incorporated herein by reference in its entirety.

STATEMENT REGARDING FEDERALLY SPONSORED RESEARCH

Not Applicable.

FIELD OF THE INVENTION

The present invention relates to an alignment guide for ensuring proper alignment or orientation when a prosthetic stem is inserted in bone.

BACKGROUND OF THE INVENTION

Stems are used in prosthetic joint implants to anchor the implant in a bone cavity. The bone is typically prepared to receive the stem by milling, drilling, or reaming the bone to form a cavity sixed and shaped for receiving the stem of the implant. The stem is driven into the prepared cavity of a bone, with its proximal end extending out of the cavity and carrying a joint bearing surface, which may be part of an assembly separately attached or coupled to the proximal stem. Many stems are fluted, i.e., they have distally extending longitudinal splines or ridges that cut their own force fit and provide greater stability and anchoring when the stem is inserted into the prepared cavity. Other stems may rely on cement fixation for a major portion of their length, but these also generally have at least some portion in the upper region that has a muting fit to the adjacent prepared bone surface. This upper portion must be placed in a precisely defined rotational orientation in order to seat properly when the stem is fully inserted.

Typically, once a fluted force-fitted stem is driven a certain distance into a prepared cavity, it becomes extremely difficult to rotate the stem to reorient the position of the upper portion. Instead, the stem must be withdrawn and reinserted, a process which can damage the bone and complicate, or increase the duration of, the operation. The stem may be aligned by marking the bone and the stem, and then matching or sighting along the respective marks to align the stem with respect to the bone as it is driven in. For example, to install an artificial hip prosthesis, the surgeon may measure the mechanical axis of the femur, perform a resection of the proximal femoral end, and then mark the plane of the mechanical axis on the periphery of the resected surface to indicate the required angular orientation of the ball joint component. The mark is then used to orient the stem as it is inserted. A drawback of this method is the imprecision of the alignment process. Because the stem seating surface is at the top of the stem, and the relevant bone markings lie at the distal end, the respective landmarks on the stem and bone are initially not in close proximity to each other. Thus, parallax and other problems associated with alignment by eye may result. Also, the stem may wander from its initial aligned position as it is being advanced into the prepared cavity.

The above-referenced patent application addresses this problem by providing prosthesis stem components having an axially-running flute or slot, or external splines, and providing a separate alignment body which nestles in the prepared cavity in a defined orientation, and keys to flute or slot such that the stem is held in the desired rotational plane as it is inserted. The alignment body or tool must be withdrawn before the stem is fully inserted, but after the stem is sufficiently well engaged to hold its own alignment. Various embodiments may control the degree of purchase of the stem and the phase where removal of the tool is effected, or may adapt those guides to different prosthesis systems. This may be done by employing a somewhat flexible polymer for the flute-engaging body, forming it with a jaw that flexes open for removal, by employing only a narrow key or guide, or by adjusting the length or diameter of the fluted region or length of slot and depth of bite to achieve dependable insertion depth and grip before tool removal is necessary.

However, there remains a need to provide tools and methods for aligning the stem of an orthopedic implant during insertion into a prepared bone cavity.

SUMMARY OF THE INVENTION

The present invention provides a method and device for orienting a prosthetic stem component as it is inserted into a prepared bone cavity. The bone is prepared by removing bone material from the bone canal and machining an opening of a predetermined shape in the bone cavity. A head alignment guide attaches to the top of the component with fixed rotational alignment and couples to a solid positioning arm that extends to a landmark at the bone to orient the stem as it is inserted into the bone cavity. The lower end of the positioning arm is oriented or placed at the bone opening so as to bring into or maintain the trunion and thus the femoral head in the required plane, which is the plane of the mechanical axis in the case of a femoral component of a hip prosthesis. The alignment guide may include a shaped or keyed lower element that engages the bone near the stem, and in this case, the positioning arm couples to the lower element without allowing rotation, so as to rigidly set the orientation of the trunion in relation to the prepared bone. The lower element may further contact and orient the distal stem. In another embodiment, the positioning arm includes a post or pin assembly which extends to an alignment mark on the proximal femur. The lower end of the pin may be pointed to, or driven into, the alignment mark scribed at the medial edge of the cut surface of the proximal femur. The guide itself clamps to the proximal portion of the component head or post, and slides along the rail or pin assembly, thus allowing the guide to remain coupled in a fixed rotational orientation as the stem is progressively advanced into the femoral canal along a path parallel to a line directed at the alignment mark. Articulation may be provided by a pivoting slide bushing assembly that rides along the pin.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

Figure 1C:
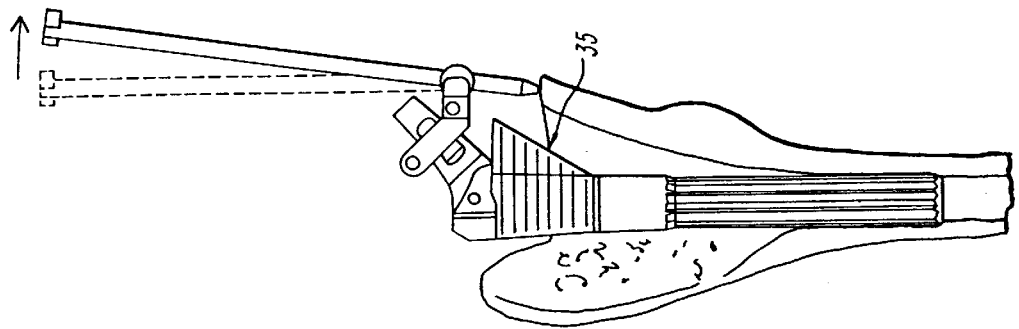
FIGS. 1A–1C are side views in section of a bone with a prepared cavity, illustrating a first embodiment of the alignment guide of the present invention, and a method of insertion using the alignment guide.
Figure 1B:
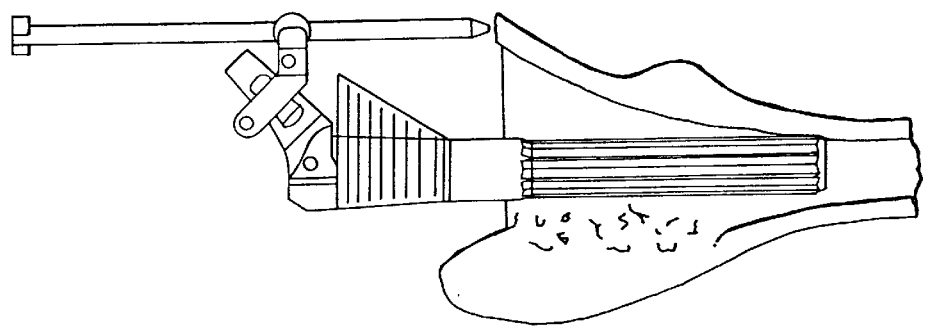
Figure 1A:
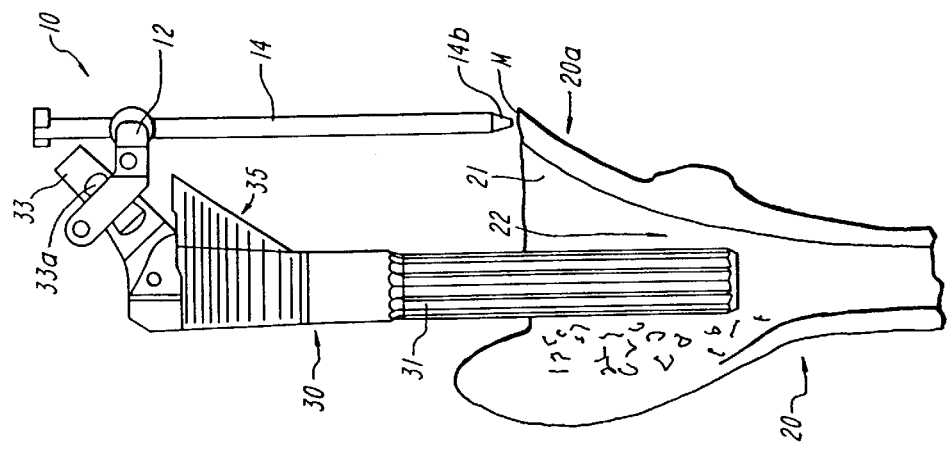

The following is a description of a first embodiment of the present invention configured for use with a hip stem implant. Referring now to FIGS. 1A–1C, an alignment guide 10 is illustrated. The alignment guide 10 comprises an upper guide assembly 12 and a positioning arm 14. The upper guide assembly 12 has a shape for engaging the upper (proximal) portion of a prosthetic stem 30 to orient it about its long axis, while the positioning arm 14 extends down to the proximal femoral end 20a, such that with the arm upright, the position of the distal end 14b of the arm determines the rotational orientation of the guide assembly 12, hence of the prosthesis head 33.

FIGS. 1A–1C show, by way of illustration, a prepared bone 20 having a machined entry 21 and a longitudinal cavity 22 formed along the canal of the bone. At least a portion of the machined entry 21 has a shape corresponding to the spout-like shape of the shoulder or upper region 35 of a femoral prosthesis stem, so that the stem must be properly oriented to seat correctly in this prepared entry portion when fully inserted in the canal. The illustrated implant stem 30 has flutes 31 distally extending along the length of the stem 30; a protrusion or proximal geometry 35 shaped to fit within the machined cavity 21 of the bone; and a post or neck 33 extending from the proximal end of the implant for receiving the ball component of a prosthetic ball and socket joint. The post 33 has a standard taper, and as shown, has been provided with flat faces 33a which, as described more fully below, are precisely positioned about a central plane corresponding to the intended alignment plane.

As will be apparent from the discussion below, the invention is broadly applicable to a femoral component prosthesis or other similar prosthesis which has a stem for insertion in the bone canal. These may include multi-component kits wherein the stem is equipped with a post or trunion as shown in FIGS. 1A–1C for receiving a ball or other component of the prosthesis assembly, and may also include castings, forgings or the like wherein the ball or other component is integral with the stem. However, as relevant to the present discussion, the prosthesis is formed with a surface in the upper region having a defined coupling portion for exactly engaging the insertion tool 10 so as to be precisely aligned therewith when so engaged. In the example illustrated in FIGS. 1–3, this is achieved by the flats 33a milled on the post 33, which for this engagement assembly 12 are angled flats spaced approximately 1–1.5 centimeters apart. By forming flats on the otherwise symmetrically tapered post, any metal-to-metal contact which might otherwise give rise to nicked or irregular surface defects is limited to regions of the post located below the surface contour of the tapered protrusion, which thus do not affect fit of the ball component that is to be subsequently locked thereon. The invention may be practiced in other forms, such as by providing an engagement region somewhat below the post, or providing a cross hole in the component head through which a pin carried by the alignment guide orients the entire assembly. Whichever mechanical engagement structure is employed, it is preferably effected in such a way as to engage the tool without looseness, but to impair neither the precision of fit nor the structural strength of the upper portion of the stem assembly and components thereof.

Figure 2:
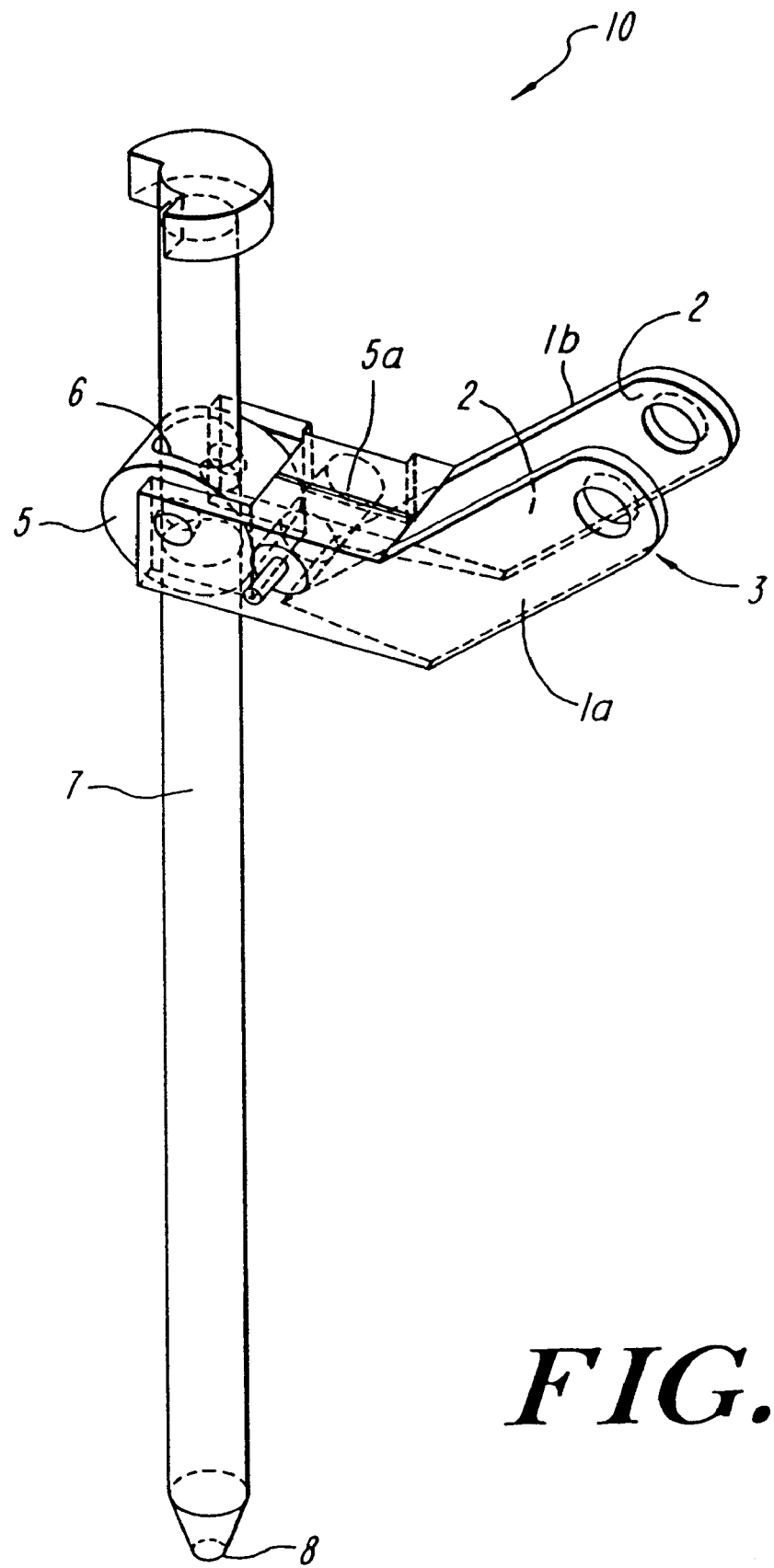
FIG. 2 illustrates the guide of FIGS. 1A–1C in greater detail.

Continuing now with the description of FIGS. 1A–1C, FIG. 1A shows the stem 30 gripped by the tool 10 and in its initial position above the prepared bone opening, before any contact with the cortical bone. At this stage, before any orientation is set, the insertion tool 10 is positioned so that its elongated arm or spike 14 extends down to the prepared proximal femoral end and is positioned exactly at an alignment mark M corresponding to the plane in which the center of the femoral ball is to lie. The spike 14 itself is visually positioned to extend vertically (in the orientation illustrated) from the end of the bone and the clamping arms of the gripping assembly 12 are tightened around the receiving flats 33a of the prosthesis post. The stem 30 is then driven into the bone opening, initially contacting and beginning bite into cortical bone as shown in FIG. 1B. At this point the insertion tool 10 provides visual feedback so as to keep the upper portion of the stem oriented in the desired plane, longitudinally aligned, and centered on axis so that as the stem is driven further down, rather than being deflected or turned off-axis by the initial asymmetric bite shown in FIG. 1B, it continues along a straight line to the seating orientation defined by the insertion tool 10. This brings the shoulder 35 into aligned seating contact with the prepared spout region 21 at the entry. FIG. 2 shows in greater detail the construction of a prototype insertion guide 10 as illustrated in FIGS. 1A–1C. As shown, the tool 10 of this embodiment has a clamp assembly 3 which rides along a rail or pin 7 which passes through closely fitting central hole 6 in the clamp assembly. The clamp assembly includes a pair of arms 1a, 1b which extend out to grip the post of the stem prosthesis at one end, and at the other end connect to a swivel body 5 which rides on the rail or pin 7. A cross-bar 5a extends between the arms 1a, 1b to further stabilize the alignment of the two arms. Each of the arms has a flat inner face 2 which is angled so as to mate closely with the angled flats on the anterior and posterior aspects of the post 33 of the stem as illustrated in FIGS. 1A–1C, thus assuring a rigid, precisely aligned grip. The rail or pin 7 has a sharp point 8 at its distal end allowing it to be driven into the femur and retain a stable position during the insertion process. Alternatively, a shoe or tab may be provided at the distal end, which may be separately pinned to fix the position of the rail 7 on the proximal femur.

Figure 3:
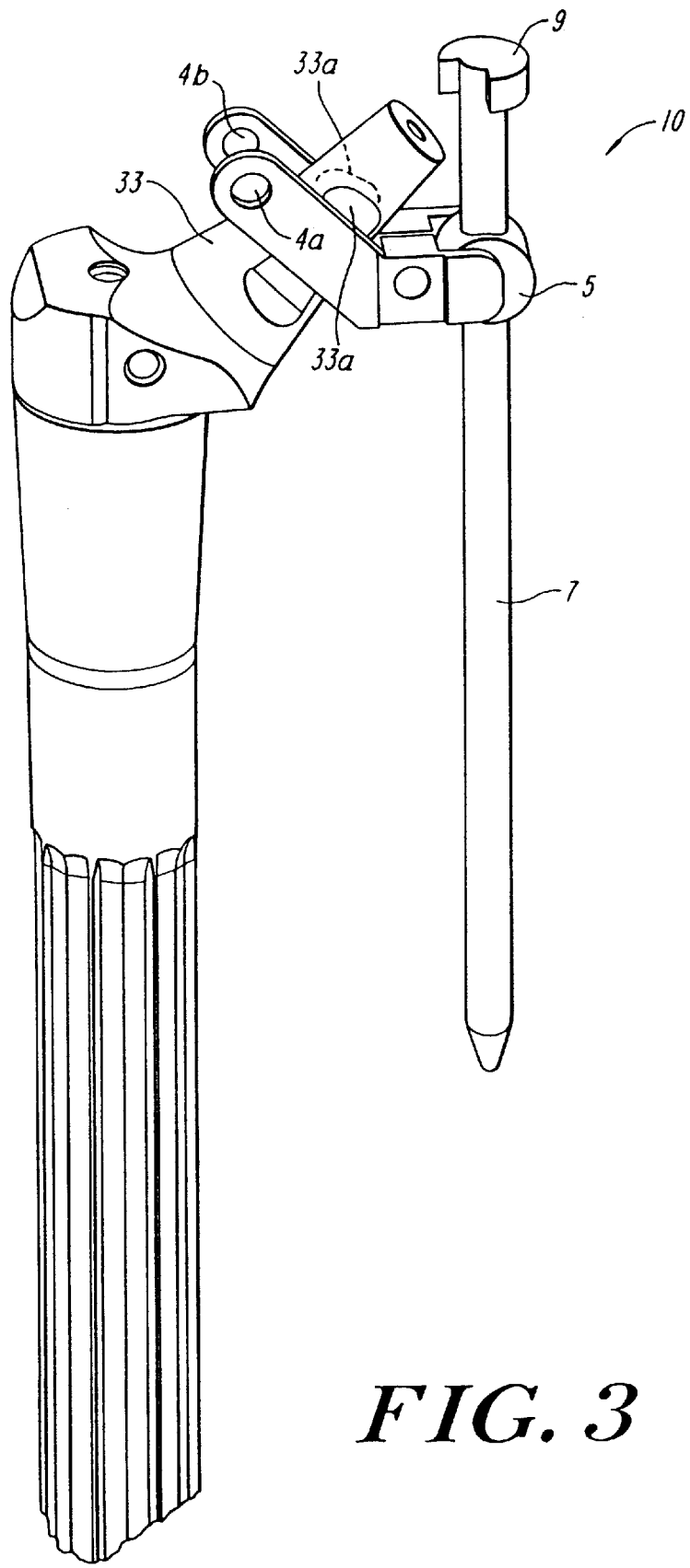
FIG. 3 is a schematic perspective view of the guide coupled to a prosthesis stem for insertion.

FIG. 3 illustrates the guide tool 10 of FIGS. 1A–1C and 2 attached to a femoral hip prosthesis stem of the type in which an essentially straight stem portion is provided as part of a kit which includes a set of modular sleeves adapted to fit various size openings of the femoral spout, and modular neck or post assemblies adapted for different sizes or offsets of the ball joint. As shown in FIG. 3, the arms of the device (1a, 1b FIG. 2) fit onto either side of the femoral neck and mate closely with the angle flats 33a on the sides of the neck 33. At the end of each arm a hole, 4a, 4b respectively, is provided through which a clamp screw allows the arms to be tightened against the flats, thus preventing any movement of clamp assembly with respect to the stem. Preferably, one of the holes 4a or 4b is threaded, while the other is somewhat enlarged so as to have clearance for the clamp bolt to pass therethrough. This bolt may be a hex head bolt for tightening with a driver, or a bolt with a winged head, thumb screw or the like for tightening by hand. With the alignment clamp 3 secured to the femoral neck, the stem 30, the clamp assembly 3 and the alignment pin 7 will all be centered on the plane of symmetry of the femoral stem.

For use, the surgeon will have prepared the proximal femur and will have made a mark or indication M (FIG. 1A) on the medial calcar wall where the stem mid-line is to be positioned. To guide insertion of the stem, the surgeon fastens the clamping arm 3 to the neck of the stem, passes the rail or pin 7 through the swivel body 5, and locates the tip of the pin 7 at the marking M made on the bone. Preferably, the surgeon then embeds the tip of the pin into the bone mark, impacting the head 9 if necessary to ensure that the pin stays in place. Thereafter, using a conventional driver, the stem is driven into the femoral canal and, as insertion proceeds, the swivel body slides down along the pin toward the designated alignment position. The arms 1a, 1b move as a unit with respect to the swivel body about an axis perpendicular to the direction of the pin 7, and the swivel body may rotate around the pin axis to allow the clamp assembly to freely track along the pin even if the angle of the pin is not exactly parallel with the axis of the bone or implant, or changes during insertion. As the stem is driven in, the sharp longitudinal splines, protrusions or flutes of the stem 30 gain purchase into the femoral canal, and rotational alignment of the stem becomes fixed in the correct orientation as insertion proceeds. Moreover, the pin provides a visual sighting line, allowing the surgeon to reorient the stems prior to the stem gaining purchase. Thus as shown in FIG. 1C, the pin provides a sight line that allows the surgeon to align the stem in two dimensions by visual sighting, while the swivel body permits the pin to displace—e.g., to swing back and to the side as the stem grips and straightens in the bone canal.

The illustrated insertion tool offers several advantages. It is mechanically simple so a surgeon may easily learn to use the device. Also, because it is configured to engage the upper portion of the stem, the stem maybe substantially entirely inserted without interference by any portion of the alignment tool. As such, the tool can be deployed throughout the entire insertion process; it need not be removed until the stem is fully seated. In addition, the guide assembly presents very little bulk extending anteriorly or posteriorly, so the instrument may be readily introduced into the constrained space of the surgical wound site.

Thus, in the broad aspects of this embodiment of the invention, a clamp assembly which grips the proximal stem ending is oriented by and slides along a locator post or rail to a designated alignment at the proximal femoral end. It will be appreciated that other forms of clamp assembly such as arrangements of articulating arms or the like may be employed, and that the rail may take other forms which, for example, may be pinned to the proximal femur by a separate pin or may otherwise couple in alignment to the bone to transfer a desired orientation to the engagement assembly at the top of the insertion tool.

Figure 4:
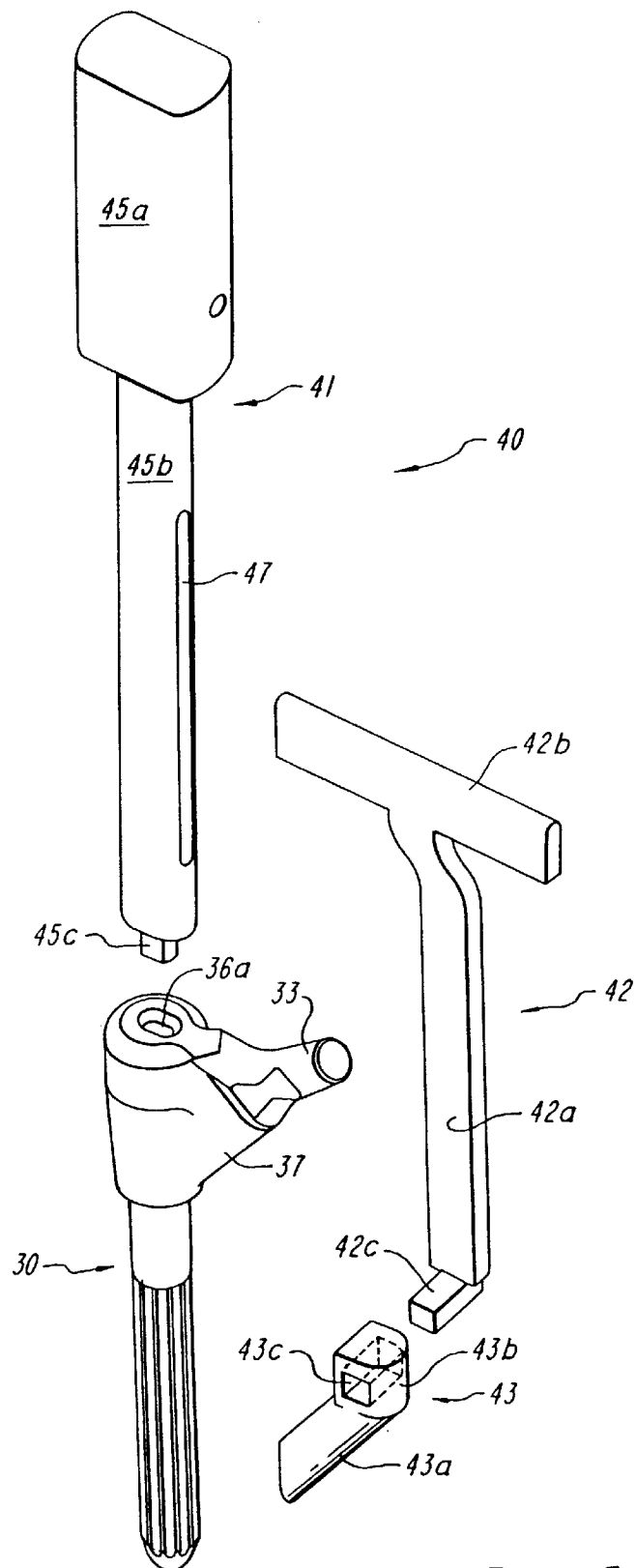
FIG. 4 is an exploded view of a second embodiment of a guide in accordance with the invention.

FIG. 4 illustrates another embodiment 40 of the invention, which in this case requires no clamp assembly and does not contact the critical assembly surfaces of the prosthesis neck 33. The embodiment of FIG. 4 includes three separate components, a driver or implant inserter 41, an orienting linkage 42 and a bone guide element 43.

In this embodiment, the upper portion of the stem 30 is engaged and oriented by the implant inserter 41 which, as illustrated, is configured with a driving handle 45a, a shaft 45b, and a protruding plug 45c at the end of the shaft that is shaped to key into a corresponding oriented socket or recess 36a formed in the top of the stem. The plug and socket fit tightly, so the stem assumes the same orientation as the handle. An orienting feature, shown as a slot 47 lies in the central plane of the shaft 45b, and runs for a vertical distance corresponding roughly to the insertable depth of the prosthesis stem 30.

In this embodiment, the prosthesis 30 has a spout portion 37, for which, as is known, the surgeon precisely mills a prepared bone spout of corresponding shape—i.e. an inclined cylindrical channel along the proper plane at the proximal femoral end. This constitutes a bone feature to which the stem is to align. This alignment is achieved by the other two components, the bone guide element or insert 43 and the orienting linkage arm 42.

The guide insert 43 is a body which is shaped to fit in the prepared bone spout. For this purpose it has an inclined, cylinder-walled lower portion 43a that nestles in the prepared channel thus defining an exact orientation plane. The guide element 43 also has an upper portion 43b that couples to the linkage arm 42 by receiving an appendage of the arm in a precision recess 43c.

As shown, this recess 43c is a rectangular cross-hole in the guide body 43, oriented in the anterior-posterior direction, and sized to fit a cross-bar 42c extending from the base of the orienting linkage arm 42. This secures the generally T-shaped linkage arm 42 so that its shaft 42a extends generally parallel to the chosen plane, and its upper T or cross arm 42b lies centered in that plane and will ride in the slot 47 of the driver/inserter 41. Each of the bar/bore or bar/slot sets 42c/43c and 42b/47 is closely fitting, so that the orientation plane of the body 43 is directly transferred to the slotted driver 41, hence to the driver recess 36a and stem 30.

In use, by impacting the handle 45a, the stem is driven into the femur exactly aligned with the spout opening. The guide body 43, which unlike the devices of the above cited patent application does not engage the stem, may be conveniently withdrawn along a generally medial-upward direction from the prepared bone cavity before the stem is fully seated.

The provision of a cross-bar 42b about which the handle is free to slide vertically and to move relatively freely in the central plane as the stem is driven in, decouples the upper and lower elements 41, 43 to some extent, and thus prevents torque or the impacts on the handle from directly reaching the thinned bone wall at the femoral entry. However the close fitting recesses 43c, 47 oriented in orthogonal directions are effective to tightly position the prosthesis along the axis in the medial plane, improving accuracy of the insertion alignment. Other linkage mechanisms, however, may be substituted to transfer the alignment from the lower bone guide to the upper stem head guide and driver.

Although the alignment guide of the present invention is described with respect to embodiments wherein the proximal stem has been fabricated or modified to have a defined, oriented geometry, which is gripped or engaged by the upper part or component of the insertion tool, the lower portion of the stem may have a conventional slot, stem flute or set of flutes, or other construction, and these need not bear any relation to the guide. In other embodiments, such lower portion may be utilized by the lower guide body 43 as a further key or reference in a manner similar to that of the insertion guides of the above-referenced patent application. It will further be apparent to those skilled in the art that various modifications may be made without departing from the character and scope of the invention. For example, the insertion guide may be used in accordance with insertion of any stem-like component having an oriented feature on the outer surface of the stem to key the insertion of the stem in a properly selected aligned position. In the upper region, the alignment guide may, instead of a clamp, have one or more indentations or protrusions effective to key the insertion orientation of the stem of the implant to that of the guide.

Particular further embodiments of the invention may employ a blade or other protrusion fitted to a slot in the stem to orient the lower guide and channel the stem into a fitted insertion position, thus allowing the stem flutes to be separately optimized for broaching or cutting a fitted passage and for securing the stem to the bone without requiring the flutes to also sustain shear forces imposed during insertion by a guiding surface. Slots, pegs or other registration features may also be substituted for the proximal holding or alignment structure.

This completes a description of the invention and representative embodiments thereof. Having been thus disclosed, further variations and modifications will occur to those skilled in the art, and all such variations and modifications are considered to be within the spirit and scope of the invention, as defined by the claims appended hereto and equivalents thereof.

What is claimed is:

1. An alignable orthopedic prosthesis system for implantation into a prepared bone cavity, said system comprising:
   (a) a prosthesis including a stem having a proximal portion, a distal portion, and an axis, and
   (b) an alignment guide including
      an upper holding portion configured to hold the proximal stem portion in fixed rotational alignment
      an alignment arm, and
      a guide portion at a lower region of the alignment arm
   configured for securing in alignment with the prepared bone cavity, said upper holding portion and said guide portion being configured for relative movement such that sliding the upper holding portion along the alignment arm effectively aligns the stem to the guide portion as the stem is inserted along said axis into the bone cavity.

2. The prosthesis system of claim 1, wherein the prosthesis comprises a stem of a prosthetic hip joint assembly.

3. The prosthesis system of claim 2, wherein the upper holding portion includes a clamp assembly configured for gripping the proximal stem portion.

4. The prosthesis system of claim 3, wherein the clamp assembly is mounted on a carriage which slides along the alignment arm as the stem is inserted.

5. The prosthesis system of claim 3, wherein the guide portion includes means for fixedly engaging the bone during stem insertion.

6. The prosthesis system of claim 5, wherein the guide portion rigidly couples with the alignment arm to orient the upper holding portion.

7. The prosthesis system of claim 1, wherein the alignment arm extends in a plane of said stem axis when the upper holding portion engages the proximal stem.

8. An alignable orthopedic prosthesis system for implantation into a prepared bone cavity, said system comprising:
   (a) a prosthesis including a stem having a proximal portion, a distal portion and an axis, and
   (b) an alignment guide including
      an upper holding portion configured to hold the proximal stem portion in fixed rotational alignment
      an alignment arm, wherein the alignment arm extends in a plane of said stem axis when the upper holding portion engages the proximal stem, and
      a guide portion at a lower region of the alignment arm configured
   for securing in alignment with the prepared bone cavity, said upper holding portion and said guide portion being configured for relative movement such that sliding the upper holding portion along the alignment arm effectively aligns the stem to the guide portion as the stem is inserted along said axis into the bone cavity, and wherein the upper holding portion is a driver which transfers its orientation to the stem and the alignment arm slides in the driver to maintain orientation of the driver during insertion.

9. A tool for aligning a stem of a prosthesis during insertion into a bone canal, such tool comprising
   an alignment arm having a length comparable to insertion length of the stem and extending from a proximal to a distal portion, said distal portion being adapted to secure in alignment with the bone canal and thereby orient the alignment arm and
   an engagement assembly adapted to tightly clamp about a portion of the stem remote from the bone canal, said engagement assembly being movable along the alignment arm so as to thereby orient the stem with respect to the bone as the stem is inserted.

10. The tool of claim 9, wherein the engagement assembly includes a clamp.

11. The tool of claim 10, wherein the clamp includes a pair of clamp arms for engaging the proximal stem, said pair of arms being pivotally attached to a sliding carriage which moves along the alignment arm.

12. The tool of claim 11, wherein the alignment arm is a spike and the distal portion is pointed so it may be driven into bone to fasten the alignment arm to bone.

13. A tool for aligning a stem of a prosthesis during insertion into a bone canal, such tool comprising
   an alignment arm having a length comparable to insertion length of the stem and extending from a proximal to a distal portion, said distal portion being adapted to secure in alignment with the bone canal and thereby orient the alignment arm and
   an engagement assembly adapted to tightly clamp about a portion of the stem remote from the bone canal, said engagement assembly being movable along the alignment arm so as to thereby orient the stem with respect to the bone as the stem is inserted,
   wherein the engagement assembly includes a driver having an orienting feature that engages and orients the stem.

14. The tool of claim 13, wherein the driver includes a slotted shaft, said shaft in use extending above a stem and being adapted for sliding movement with respect to the alignment arm.

15. The tool of claim 14, further comprising a guide body adapted for seating against a prepared bone surface and having a recess for receiving and orienting said alignment arm distal portion.

16. An alignment tool for driving a femoral stem prosthesis into a prepared femoral canal such that the prosthesis seats against a prepared bone surface, such tool comprising
   an orienting assembly for engaging a proximal stem and setting an orientation of the stem
   an elongated member having a proximal region and having a distal end alignable to the proximal femur, said member extending along a length comparable to insertable length of the stem,
   said elongated member maintaining orientation of the orienting assembly, and the orienting assembly sliding along the elongated member so that alignment of the distal end of the elongated member at a proximal region of femoral bone is transferred to and maintained by the stem as the orienting assembly moves along the elongated member during insertion of the stem.

17. The tool of claim 16, wherein the orienting assembly comprises a driver.

18. The tool of claim 17, wherein the elongated member comprises a T-bar having an upper arm lying in a first plane, and a lower protrusion extending transverse to said first plane.

19. The tool of claim 16, wherein the orienting assembly comprises a clamp.

* * * * *